United States Patent [19]
Ugelstad et al.

[11] Patent Number: 4,654,267
[45] Date of Patent: Mar. 31, 1987

[54] MAGNETIC POLYMER PARTICLES AND PROCESS FOR THE PREPARATION THEREOF

[75] Inventors: John Ugelstad; Turid Ellingsen; Arvid Berge, all of Trondheim, Norway; Oskar B. Helgee, Mölnlycke, Sweden

[73] Assignee: SINTEF, Trondheim, Norway

[21] Appl. No.: 571,878

[22] PCT Filed: Apr. 22, 1983

[86] PCT No.: PCT/NO83/00014
§ 371 Date: Dec. 23, 1983
§ 102(e) Date: Dec. 23, 1983

[87] PCT Pub. No.: WO83/03920
PCT Pub. Date: Nov. 10, 1983

[30] Foreign Application Priority Data

Apr. 23, 1982 [NO] Norway ................................ 821327
Nov. 16, 1982 [NO] Norway ................................ 823748

[51] Int. Cl.$^4$ .......................... H01F 1/20; B32B 15/08
[52] U.S. Cl. ..................................... 428/407; 428/900; 252/62.54; 521/55; 525/328.2; 525/330.4; 525/330.5; 525/332.2; 525/333.5; 525/333.6; 525/344; 525/374
[58] Field of Search .......................... 252/62.52, 62.54; 427/128, 130; 428/407, 692, 693, 900; 521/55; 525/362, 371, 360, 328.2, 330.4, 330.5, 332.2, 333.5, 333.6, 344, 374; 523/202, 204, 210; 526/329.2

[56] References Cited

U.S. PATENT DOCUMENTS 4,001,288  1/1977  Gable et al. ................ 252/62.52
4,018,691  4/1977  Neal ............................ 252/62.52 X
4,123,396  10/1978 Rembaum et al. ......... 521/55 X
4,339,337  7/1982  Tricot et al. ................ 252/62.54
4,438,179  3/1984  Sole ............................ 428/407

OTHER PUBLICATIONS

Hackh's Chemical Dictionary, J. Grand (ed.), McGraw-Hill Inc., p. 457 (1969).

Primary Examiner—Joseph L. Schofer
Assistant Examiner—F. M. Teskin
Attorney, Agent, or Firm—Wenderoth, Lind & Ponack

[57] ABSTRACT

Magnetic polymer particles prepared by treating compact or porous polymer particles with a solution of iron salts and, if desired, salts of other metals which are capable of forming magnetic ferrites, in which the solution swells or penetrates into the particles. Iron hydroxide and other metal hydroxides, if employed, are precipitated, e.g. by raising the pH value, and the particles are optionally heated. In the iron salts used, the ratio between di- and trivalent iron is suitably such that magnetic iron oxide is formed directly. It is also possible to use oxidizing or reducing groups or additives to obtain such a ratio. When other metal salts are used in addition to iron salts, the operation is carried out in the same manner. For instance, when $Mn^{++}$, $Co^{++}$ or $Ni^{++}$ salts are used in addition to $Fe^{++}$ salts, the divalent iron is oxidized to trivalent so that magnetic ferrite is obtained. The polymer particles which are treated with metal salts preferably contain metal-binding groups. Such groups are incorporated e.g. by using monomers which contain said groups for the preparation of the polymer particles, or the groups are incorporated in the polymer particles prepared.

The magnetic polymer particles are spherical and have a uniform concentration of magnetic material. They may be used for medical, diagnostic or other purposes.

9 Claims, No Drawings

MAGNETIC POLYMER PARTICLES AND PROCESS FOR THE PREPARATION THEREOF

The present invention relates to magnetic polymer particles and a process for the preparation thereof. It has been tried to use magnetic polymer particles within several fields of biochemistry and medicine. They have been tried as carriers for pharmaceutical preparations since they, due to their magnetic properties, are capable of transporting the preparations to the desired location in the body. Magnetic particles also have other practical applications and have been used within diagnostics since it is possible to replace separation of particles by means of centrifugation by the much simpler method of magnetic extraction. Further, magnetic particles have been used for cell separation and as carriers for enzymes. Of more technical applications may be mentioned toners for copying purposes.

Previous processes for preparing particles containing for instance magnetic iron oxide (magnetite) have started from magnetite $Fe_3O_4$. In several ways it has been tried to coat the magnetite particles with polymeric material to obtain polymer particles containing magnetite.

A commonly used method employs magnetite powder which is mixed mechanically with molten polymer. After this treatment the polymeric material containing magnetite is finely divided. This provides particles having an uneven shape and being of different size. Particles prepared in this manner are often used as toner, but the uneven shape is undesired since it will result in uneven and unsharp edges on the characters.

Another method employs finely divided magnetite to which vinyl monomer and initiator are added in water to form polymer around the magnetite grains. This will also provide magnetic particles having an undefined and highly variable size and shape. Further, only some of the particles will be magnetic, and the content of magnetite in the particles is usually very unequal. Other methods employ the admixture of albumin and other proteins with magnetite and vigorous stirring in water with emulsifier to form drops which contain magnetite and protein. Another method comprises treatment of swelling polymer particles with finely divided magnetite to obtain magnetite on and possibly some inside the particles.

The fact that magnetite is used will, even if it is employed in very finely divided form, represent great limitations with respect to the type and the size of the particles. A real diffusion of molecular material into the particles or into pores of the particles will not take place. With solid, porous particles, very large pores would be necessary, and accordingly, large particles, so that magnetite grains are deposited not only on the surface of the particles. With highly swelling particles it is possible to get some magnetite into the particles mechanically, but the magnetite will essentially be deposited on the surface and result in a very uneven surface.

According to the process of the present invention iron is introduced into the particles in the form of salts and is then converted to magnetic iron oxide which to a great extent will be magnetite ($Fe_3O_4$) or oxides having corresponding magnetism.

For many of the above purposes, the particles prepared according to the invention will be advantageous since they are spherical and have an even concentration of magnetic material which may be varied as desired within wide limits. In particular, the process provides the possibility for preparing monodisperse particles of desired size, compact as well as porous.

The process according to the present invention is suitable for compact as well as porous polymer particles and may be used for the preparation of magnetic polymer particles of all sizes. In particular the process is suitable for the preparation of particles in the range 0.5–20 $\mu$m, but it may also be used for the preparation of particles smaller than 0.5 $\mu$m and larger than 20 $\mu$m in diameter. A great advantage of the process is that it allows all of the particles to have the same concentration of magnetic iron oxide. When monodisperse polymer particles are used as starting material, the process will in particular provide monodisperse magnetic polymer particles which all contain the same amount of magnetic iron oxide.

According to the invention there is provided a process for preparing magnetic polymer particles. The process is characterized in that solutions of iron salts and optionally salts of other metals which may form magnetic ferrites, in water or in a mixture of water and water-soluble organic solvents or in organic solvents, are mixed with polymer particles in dry form or dispersed in water or in a mixture of water and water-soluble organic liquids or in organic liquids, and the metals are precipitated in the form of hydroxides, for instance by raising the pH value, and, if desired, the particles are heated.

In the following description of the new process for the preparation of magnetic polymer particles, the preparation of magnetic particles containing magnetite $Fe_3O_4$, which may also be described as ferroferrite, $FeFe_2O_4$, is described in detail.

As it will be seen, it is also possible to use some of the described embodiments for the preparation of polymer particles containing other magnetic ferrites such as manganoferrite $MnFe_2O_4$, cobalt ferrite $CoFe_2O_4$ and nickel ferrite $NiFe_2O_4$. Normally, the content of magnetic ferrite in the particles will be above 5%.

According to the invention there are particularly used compact or porous particles which contain groups which may have the effect that the iron salt is drawn into the particles and is possibly bound therein. These groups may be incorporated in the particles by preparing the polymer from a monomer containing these groups. Examples of monomers which have been found to be particularly suitable, are dimethylamino-ethylmethacrylate, N-(dimethylaminopropyl)-methacrylic amide and vinyl pyridine which will bind the iron salts with coordinate bonding. Other examples of suitable monomers are such which contain ethylene oxide groups ($-CH_2-CH_2-O-$) or alkylene imine groups ($-CH_2-CHR'-NH-$, in which $R'=H$ or alkyl).

It is also possible to bind the iron by means of ionic bonds. By having acid groups on and inside the particles, the iron may be transported from the outer phase of the dissolved iron salt to be bound to these groups. Examples of monomers which will provide such acid groups are methacrylic acid, p-vinyl benzoic acid and maleic anhydride. The iron salt-binding groups may also be attached to the premade polymers. Thus, it is possible to prepare a copolymer from a monomer mixture which essentially consists of vinyl monomer with epoxy group(s) such as glycidyl methacrylate:

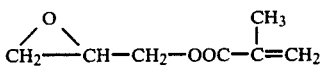

By treating the final polymer with substances which react with epoxy groups and which contain N-groups, said groups will become covalently bonded on and inside the particles. It is for instance possible to treat polymer particles containing epoxy groups with ethylene diamine to form —$CH_2$—NH—$CH_2$—$CH_2$—$NH_2$ groups, or with ethylene oxide group-containing substances such as $NH_2$—R—$(CH_2CH_2O)_nR'$ or HOOCR-COO$(CH_2CH_2O)_nR'$, wherein R is a suitable aliphatic or aromatic group, R' is hydrogen or alkyl, and n is an integer from 1 to 500, to introduce —$(CH_2$—$CH_2$—$O)_nR'$ groups. For the introduction of —$(CH_2$—$CH$—R'—NH—$)_nH$ groups it is for instance possible to react polymer particles containing —COOH groups with alkylene imine compounds, to form —CO—O—(C-$H_2$—CHR'—NH—$)_nH$ groups. For the introduction of amino and/or imino groups in the case the polymer contains ester groups such as —COOR' in which R' is an alkyl group, it is possible to carry out an aminolysis with an organic amine which contains more than one amino group. Thus, by aminolysis of a polymer containing —COOR' groups with diethylene triamine, —CONH—$CH_2CH_2NHCH_2CH_2NH_2$ is formed. These reactions may also have the effect that the particles become more hydrophilic and will swell with $H_2O$ so that iron salts are bound inside the particles.

Another method for the introduction of iron-binding groups comprises the introduction of —$NH_2$ groups or —$CH_2$—$NH_2$ groups on the benzene nucleus in polymer particles prepared by polymerization of a monomer which to a considerable extent contains benzene rings such as styrene and divinylbenzene.

Further, after the introduction of —$CH_2NH_2$ onto the benzene nucleus, it is possible to introduce

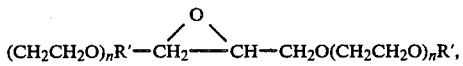

in which R' and n are as above. It is also possible to introduce $CH_2Cl$ groups on the benzene nucleus and react these groups with HO$(CH_2CH_2O)_nR'$ or $NH_2(CH_2CH_2NH)_nNH_2$.

The ethylene oxide chain may also be introduced into the final polymer by reacting such a polymer which contains acid groups, with the epoxide

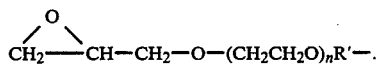

On polymers which contain benzene nuclei, it is possible to introduce 13 NH—$NH_2$ groups onto the benzene nucleus. If particles made from acrylates are treated with hydrazine, —CONH—$NH_2$ groups are formed.

Similarly, acid groups may be introduced into the final polymer particles. This may for instance be obtained by hydrolyzing a polymer which contains ester groups. Similarly, by known methods it is possible to introduce sulphonic acid groups and carboxylic acid groups into the polymer which has been prepared from styrene and/or styrene-derivatives and admixture of these with divinyl benzene. By (a) preparation of a polymer from a monomer containing N-groups, hydroxy, ethylene oxide or acid groups, by (b) posttreatment of an epoxide group-containing polymer with substances such as ethylene diamine, by (c) posttreatment of a polymer containing carboxylic acid groups with alkylene imine, by (d) posttreatment of a polymer which contains ester groups, with an organic amine having more than one —$NH_2$ or —NH group, and similarly by (e) posttreatmentof acrylate particles with hydrazine, it is possible to obtain particles which swell in water or a mixture of water and organic solvents, which will promote the introduction of iron salt into the particles and have the effect that more iron salt is bound. The polymer particles may also be prepared as porous particles having a macroreticular structure, i.e. a firm pore structure. In this case the iron salts may be bound in a single layer to the surface inside the pores, but since this surface is very large, a relatively high content of iron inside the particles will nevertheless be obtained. In other cases the iron compound may to a greater or smaller extent fill the pores. Porous particles having a macroreticular structure may be prepared by groups which bind iron salts directly, or the particles may be posttreated for the introduction of said groups as described above.

In the case of porous particles having a large surface, it is also possible to introduce iron salt into the particles by coating the interior surface with substances which contain iron-binding groups and which are bound strongly to the surface, before the addition of iron salts, or said substance is added together with the iron salt. Such substances are for instance polyamine amide with limited chain length or substances which contain one or preferably more acid groups or acid groups combined with other groups which provide a strong bonding of iron salts. With porous particles it is possible to use iron salts in which the anionic group is so large and is so hydrophobic that it is bound directly to the interior surface by physical adsorption.

After the particles and the iron salts have been mixed, the pH is raised and iron hydroxide is formed. If one has groups which bind iron salts and these are primary, secondary or tertiary amines, polyethylene oxide groups or anions of acids, one will preferably add a mixture of a divalent and trivalent salt in a ratio which will result in an amount of Fe(OH)$_2$ and Fe(OH)$_3$ after precipitation which is such that the mixture may result in Fe$_3$O$_4$. It is then a particular and important feature that the particles contain groups which attract the iron salt from the outer phase and bind it on and inside the particles so that by raising the pH there will not be an essential precipitation of Fe(OH)$_3$ in the outer phase outside the particles.

If the particles which are swollen by the liquid in the outer phase or the porous particles filled with the liquid from the outer phase do not contain groups which bind iron salts, only some of the iron salt will be found inside the particles, and by raising the pH an essential part of the added trivalent iron salt will then be precipitated in the outer phase, which would have the effect that less magnetic iron oxide would be formed inside the particles and also that an essential amount of magnetic iron oxide would be present in the outer phase with subsequent complicated purification processes.

In the case of particles prepared with some polyvinyl monomer (i.e. a monomer containing several vinyl groups, such as divinyl benzene), it is possible to swell the particles in organic solvents, and iron salts which are soluble in these solvents may then be introduced. Also in this case it is advantageous that the particles contain groups which will bind the iron salts so that upon the subsequent transfer of the particles to water the iron salts will remain bound inside the particles. If iron salts containing hydrophobic anions are used, such as iron laurate, the iron compounds will remain in the particles when these are transferred to water, and specific iron-binding groups are not of the same importance. This will also be the case when solid, porous particles having hydrophobic structure are used.

If the iron-binding groups are hydrazine groups —N-H—NH$_2$, a trivalent iron salt is preferably used. Even in this case it is therefore important that the trivalent iron salt is bound on and inside the particles before the pH is raised to form Fe(OH)$_3$.

In a particular embodiment of the present invention porous particles containing NO$_2$ groups bound to the benzene nuclei are prepared. These particles may for instance be prepared by the preparation of porous particles from nitrostyrene and divinyl benzene in an ordinary manner, i.e. in the presence of inert solvents which are removed after the polymerization, or porous particles may be prepared from styrene or styrene derivatives and divinyl benzene, and then nitro groups are introduced onto the benzene groups according to ordinary methods.

In these cases where nitro groups are present in porous particles, only divalent iron salt is used. The nitro groups will only to a small extent have the effect that the iron salt is transported from the outer phase into the particles. However, when the pH is raised and Fe(OH)$_2$ is formed, an oxidation will take place inside the particles by means of —NO$_2$ groups which will oxidize Fe(OH)$_2$ to Fe(OH)$_3$ in such an amount that the ratio between di- and trivalent iron corresponds to that of Fe$_3$O$_4$. Thereby more Fe(OH)$_2$ is constantly transferred from the outer phase to the pores of the particles. This process is accelerated by the fact that the oxidation of Fe(OH)$_2$ by —NO$_2$ groups has the effect that the —NO$_2$ groups are converted to groups in which the nitrogen has a higher electron density and thereby acquires an increased ability to bind iron salt.

The same principle, i.e. oxidation of added divalent iron salt with an oxidizing nitro component, may also be carried out when the oxidizing nitro component is —ONO$_2$ groups or ONO groups.

These groups may for instance advantageously be attached to porous particles which contain a large number of hydroxy groups on the surface by allowing these to react with HNO$_3$ or HNO$_2$.

Examples of such polymers are macroreticular porous particles prepared with a substantial part of hydroxyethylmethacrylate in the monomer mixture. Other examples are porous particles having an essential content of glycidyl methacrylate in the monomer mixture. In this case the epoxy groups

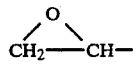

may be reacted directly with HNO$_3$ or HNO$_2$, or hydroxy groups may be introduced by reacting epoxy groups with for instance aminoethanol.

In the methods involving the formation of Fe(OH)$_2$ and Fe(OH)$_3$ on and in the particles it is often found that already by the formation of this mixture, the particles have become magnetic directly. A more complete magnetization with formation of Fe$_3$O$_4$ is obtained by heating. Usually it is sufficient to heat the particles in aqueous dispersion. to a temperature below 100° C. The particles may be isolated by centrifugation or filtration or may be extracted with a magnet and dried, and may possibly also be heated in dry condition.

If hydrazine groups are used, it is possible to use pure trivalent salt, and Fe(OH)$_3$ is then formed and is by means of the hydrazine groups reduced to a mixture of divalent and trivalent iron corresponding to the same oxidation stage as in magnetite. This is preferably carried out at temperatures above 100° C.

If either di- or trivalent iron hydroxide in or on the particles has been formed in any of the above processes, it is also possible to convert the hydroxide to the desired mixture of di- and trivalent iron hydroxide. Divalent iron hydroxide may for instance be oxidized by the addition of a suitable oxidizing agent, such as nitrate ion or an organic nitro compound, or the oxidation may for instance be carried out by blowing oxygen therethrough. Trivalent iron hydroxide may be reduced with a suitable reducing agent, such as hydrazine.

In magnetite, Fe$_3$O$_4$, the ratio between di- and trivalent iron is 1:2. It is therefore suitable to use a mixture of iron salts with approximately this ratio between di- and trivalent salts when no normally reducing/oxidizing groups are present. If the ratio Fe$^{++}$/Fe$^{+++}$ after the rise of the pH is essentially above 1:2, the formed hydroxides are oxidized, and if it is essentially below 1:2 they are reduced to form magnetic iron oxide.

In the processes described above in which a mixture of 2- and 3-valent iron salt or a 2-valent iron salt which is oxidized, is used, ferroferrites FeFe$_2$O$_4$ (=Fe$_3$O$_4$) are formed. In these cases it is also possible to use a mixture of iron salts with other metal salts which will provide other types of magnetic ferrites. Thus, according to the same principles it is also possible to form manganoferrite, MnFe$_2$O$_4$, cobalt ferrite, CoFe$_2$O$_4$ or nickel ferrite NiFe$_2$O$_4$. If a mixture of a water-soluble salt of a 2-valent metal, such as MnX$_n$, CoX$_n$ or NiX$_n$, in which X is a 2/n-valent anion (n=2, 1, ⅔ or ½, particularly 1 or 2) and a water-soluble salt of 3-valent iron is used, the salt mixtures are precipitated as hydroxides inside the particles and are then heated to a suitable temperature to form the corresponding magnetic metal ferrites. If a salt of 2-valent iron is used in admixture with the other metal salt, the divalent iron in the form of iron hydroxide inside the particles is oxidized to trivalent iron under conditions which provide the desired metal ferrite. The oxidation may take place by means of oxidizing groups such as —NO$_2$, —ONO or —ONO$_2$ which have been introduced onto the polymers, or it may take place by the addition of suitable oxidizing agents. In this case it is possible to obtain a mixture of ferroferrite with other ferrites, MeFe$_2$O$_4$, in which Me represents Co, Ni or Mn. An advantage of using a mixture of iron salt with other metal salts is that in this case there is no risk of overoxidation of the iron, since in that case there will only be formed MeFe$_2$O$_4$ at the expense of FeFe$_2$O$_4$.

The polymer particles used as a starting material for the preparation of magnetic particles may in principle be prepared by any methods which are known for the preparation of dispersions of polymeric particles. This includes a preparation by ordinary emulsion polymerization, in which the monomer is added to water with or without emulsifier, polymerization is carried out by means of a water-soluble initiator, and the particles are initiated in the aqueous phase. The method will result in particles in the range up to about 0.6 μm in diameter. The size and the monodispersity increase with decreasing amount of emulsifier. The particles may also be prepared by initiation in drops, which may be obtained in different ways. It is for instance possible to homogenize a mixture of monomer with a small amount of a water-insoluble material having a water-solubility less than $10^{-3}$ g/l $H_2O$ with water and emulsifier, which will provide stable monomer emulsions, and then polymerize with addition of initiator and heating. The water-insoluble substance used may be a water-insoluble monomer. If desired, it is possible to use an oil-soluble initiator which is added together with the monomer before the homogenization. Possibly this initiator may in itself serve as the water-insoluble substance which provides stable monomer emulsions. By this method initiation may take place exclusively inside the drops.

It is also possible to homogenize in a first step a water-insoluble substance having a water-solubility less than $10^{-3}$ g/l $H_2O$ with water and emulsifier. Then monomer is added which will diffuse into the drops of water-insoluble substance and polymerize by means of water-soluble initiator or oil-soluble initiator added together with or after the monomer and which has such a high water-solubility that it just like the monomers may diffuse through the water and into the drops of the water-insoluble substance. Also in this case the water-insoluble substance used during the homogenization may be an initiator.

The polymer particles may also be prepared by seed processes. In this case a seed of polymer particles dispersed in water is used, possibly a mixture of water and an organic solvent which is soluble in water, and the desired monomers are introduced into the polymer particles before polymerization either with a water-soluble initiator or with an oil-soluble initiator added together with or after the monomers. In many cases, particularly for the preparation of larger particles, it is possible to use a seed technique which comprises the preparation in a first step of particles which in addition to the polymer molecules also contain a water-insoluble substance having a relatively low molecular weight. Such a method has been described in Norwegian patent No. 142.082. When the water-insoluble substance having a water-solubility of less than $10^{-3}$ g/l $H_2O$ and having a relatively low molecular weight is present in the particles, these are as described in said patent capable of absorbing much more monomer than ordinary polymer particles.

A specific embodiment of this method which has also been found to be favourable for the preparation of polymer particles which are later converted to magnetic particles, comprises that the water-insoluble substance used for swelling the polymer particles in the first step, is an oil-soluble initiator which is used for polymerization after the monomer has diffused into the particles.

The preparation of polymer particles by seed technique is particularly favorable when it is desired to prepare spherical magnetic particles which are monodisperse and which will therefore also contain the same amount of magnetic ferrite in each particle. In this case one starts with a monodisperse seed, i.e. a polymer dispersion where all the particles have approximately the same size, for instance a standard deviation of less than 5%. The standard deviation for the content of magnetic ferrite will then normally be less than 10%. The polymeric particles may also be prepared by ordinary suspension polymerization. In this case large particles are obtained directly, but with a broad size-distribution.

The particles prepared according to the above methods by polymerization in drops or swelled particles, may be obtained as porous particles by using ordinary methods which involve the use of a mixture of monomers at least one of which is a polyvinyl compound, and in addition inert solvents for the monomers are present, which are removed after the polymerization. For the preparation of the polymer particles it is possible to use ordinary vinyl monomers and polyvinyl monomers and mixtures thereof. Examples of vinyl monomers which are used, are styrene and styrene derivatives, maleic anhydride, acrylates and methacrylates such as methylacrylate, methylmethacrylate, ethylacrylate, ethylmethacrylate, butylacrylate and butylmethacrylate, and vinyl esters such as vinyl acetate. Examples of polyvinyl monomers which may be used, comprise divinyl benzene, ethylene glycol dimethacrylate, trimethylolpropane trimethacrylate and adipic acid divinyl ester. As emulsifier ordinary ionic or non-ionic emulsifiers may be used. As initiator water-soluble initiators such as potassium persulphate and $H_2O_2$ or oil-soluble initiators such as azobisisobutyric nitrile and benzoyl peroxide may be used. As inert materials which are used to stabilize emulsions of monomer or to increase the swelling capacity of the polymer particles, one may use substances which are disclosed in Norwegian patent Nos. 139.410 and 142.082. Examples are alkanes having a chain length above 10 C-atoms, halogenated alkanes, esters and diesters such as dioctyl adipate. Examples of water-insoluble initiators used as additive for increasing the swelling of particles with monomer as well as for polymerization, are dioctanoyl peroxide and didecanoyl peroxide.

The preparation of dispersions of polymers in water may also be carried out by dissolving the polymer in a solvent which is slightly soluble in water and then mixing the solution of the polymer with water and emulsifier and subjecting the mixture to strong shear forces, for instance by means of ultraturrax stirrer or pressure homogenizer, to obtain a fine emulsion of the polymer solution in water with varying drop size. By removing the solvent, for instance by evaporation, there will be formed a finely divided dispersion of polymer particles in water.

The incorporation of metal salts in the particles may take place before or after the removal of the organic solvent. In this case where the polymer dispersion is prepared from a final polymer it is irrelevant how the polymer has been prepared. It may have been prepared by radical polymerization of vinyl monomers as described above, but it may also have been prepared by any process which results in polymers, such as cationic and anionic polymerization, stepwise addition polymerization and condensation polymerization.

EXAMPLE 1

100 ml of methylmethacrylate, 90 ml of glycidyl methacrylate, 10 ml of ethyleneglycol dimethacrylate and 1750 ml of $H_2O$ were mixed in a reactor. The mixture was then subjected to rapid stirring for 30 min. Then, 2.0 g of $(NH_4)_2S_2O_8$ dissolved in 50 ml of water were added. The temperature was raised to 65° C., and polymerization was carried out for 6 hours. After polymerization a latex containing 10% of polymer, particle size 0.2–0.3 µm, was obtained.

100 ml of the latex were treated with 100 ml of ethylene diamine at 80° C. for 3 hours. After the reaction, excess ethylene diamine was removed by dialysis for 10 days, with change of water every day.

Elementary analysis showed that the particles contained 4.6 percent by weight of N. 50 ml of dialyzed latex containing 5 g of particles treated with ethylene diamine were cooled down to 10° C.

811 mg (3.0 mmole) $FeCl_3.6H_2O$ were dissolved in 20 ml of water and cooled down to 10° C. Similarly, 338 mg (1.7 mmole) $FeCl_2.4H_2O$ were dissolved in 20 ml of water and cooled down to 10° C. The two iron chloride solutions were combined and then mixed with the latex in a rotating container which was rapidly evacuated down to 10 mm Hg. After 20 minutes 10 ml cold (10° C.) ammonia solution (25%) were added by suction. The vacuum was then eliminated, and the temperature was raised to 80° C. After 30 minutes at 80° C., the mixture was cooled and the particles separated from the solution by centrifugation. The particles were washed several times with water to remove excess ammonia and ammonium chloride formed. After this treatment the particles contain magnetic iron oxide. The iron content in the particles was found to be 4.9%.

EXAMPLE 2

200 ml of methylmethacrylate, 10 ml of stearylmethacrylate, 75 ml of glycidylmethacrylate, 15 g of ethylene glycoldimethacrylate, 1500 ml of $H_2O$ and 4.5 cetyltrimethylammonium bromide were homogenized to an emulsion with a drop size of 0.2–0.4 µm. The mixture was transferred to a 4 l reactor. 1.9 g of $NaHCO_3$ and 1150 ml of $H_2O$ were added. The reactor was evacuated and filled with 99.9% $N_2$ in several operations, and then 9 g of $H_2O_2$ (30% active) dissolved in 50 ml of $H_2O$ were added. The temperature was raised to 60° C. After the polymerization a latex having a particle size of 0.2–0.4 µm and a solids content of 9.5% was obtained.

Treatment with ethylene diamine for the introduction of primary amino groups was carried out as described in example 1. After this treatment the particles contained 2.8% N.

To 30 ml of dialyzed latex containing 3 g of particles treated with ethylene diamine were added iron chloride and ammonia solution as described in example 1. In this case 514 mg (1.9 mmole) of $FeCl_3.6H_2O$ in 20 ml of water, 219 mg (1.1 mmole) of $FeCl_2.4H_2O$ in 20 ml of water and 8 ml of ammonia solution (25%) were added. The further treatment and recovery of the particles were carried out as described in example 1.

The final particles contain magnetic iron oxide. The iron content in the particles was found to be 5.2%.

EXAMPLE 3

10 ml of hexadecane, 50 ml of $H_2O$ and 0.15 g of Na-lauryl sulphate were homogenized to an emulsion with a drop size of 0.2–0.7 µm. The mixture was transferred to a reactor. 800 ml of $H_2O$ and 1.0 g of Na-lauryl sulphate were added. A mixture of 130 ml of methylmethacrylate, 60 ml of glycidylmethacrylate, 10 ml of ethylene glycoldimethacrylate and 4 g of azo-bisisobutyronitrile was added slowly under stirring. After 2 hours the temperature was raised to 60° C. The polymerization takes place for 6 hours, and a latex having a particle size of 0.5–2 µm and a solids content of 19% is obtained. Treatment with ethylenediamine for the introduction of primary amino groups was carried out as described in example 1. After the reaction, the particles were separated and washed several times with water in a centrifuge to remove excess ethylene diamine.

Elementary analysis showed that the particles contained 3.5% N.

To 25 ml of a latex containing 2.9 g of particles treated with ethylene diamine there were added iron chloride and an ammonia solution as described in example 1. In this case 649 mg (2.4 mmole) of $FeCl_3.6H_2O$ dissolved in 20 ml of water, 278 mg (1.4 mmole) of $FeCl_2.4H_2O$ dissolved in 20 ml of water and 10 ml of an ammonia solution (25%) were added. The further treatment and the recovery of the particles were carried out as described in example 1.

The final particles contain magnetic iron oxide. The iron content in the particles was found to be 6.6%.

EXAMPLE 4

10 ml of dioctanoylperoxide, 30 ml of $H_2O$ and 0.03 g of Na-laurylsulphate were homogenized to an emulsion having a drop size of 0.2–0.7 µm.

The mixture was transferred to a reactor. 800 ml of water and 1.0 g of Na-laurylsulphate were added. Under stirring at 25° C. a mixture of 110 ml of methylmethacrylate, 90 ml of glycidylmethacrylate and 10 ml of ethylene glycoldimethacrylate was added slowly. After 2 hours the temperature was raised to 65° C. When the polymerization was terminated, a latex having particle size of 0.5–2 µm and a solids content of 19% was obtained. The treatment with ethylene diamine for the introduction of primary amino groups was carried out as described in example 3. Elementary analysis showed that the particles contained 4.6% N.

To 30 ml of a latex containing 2 g of particles treated with ethylene diamine there were added iron chloride and an ammonia solution as described in example 1. In this case 514 mg (1.9 mmol) of $FeCl_3.6H_2O$ in 20 ml of water, 219 mg (1.1 mmole) of $FeCl_2.4H_2O$ in 20 ml of water and 10 ml of an ammonia solution (25%) were added. The further treatment and the recovery of the particles were carried out as described in example 1.

The final particles contain magnetic iron oxide. The iron content in the particles was found to be 7.5%.

EXAMPLE 5

10 ml of dioctanoyl peroxide, 30 ml of $H_2O$ and 0.03 g of Na-laurylsulphate were homogenized to an emulsion with a drop size of 0.2–0.7 µm. The mixture was transferred to a reactor. 800 ml of water and 1.0 g of Na-laurylsulphate were then added. Under stirring at 25° C. a mixture of 40 ml of glycidylmethacrylate, 40 ml of ethylene glycoldimethacrylate and 120 ml of cyclohexanol was slowly added. After 2 hours the temperature was raised to 60° C. After the polymerization was ended, a latex having a particle size of 0.5–2.0 µm was obtained. The cyclohexanol was removed by washing several times with water and isopropanol. After drying a porous powder having a specific surface of 115 m²/g (BET-method) was obtained.

10 g of the porous particles were treated with 100 ml of ethylenediamine at 80° C. for 3 hours. Unreacted ethylene diamine was removed by centrifugation and several washings with $H_2O$. Elementary analysis showed that the particles contained 5.8% N. 3 g of dry particles treated with ethylenediamine were added to 20 ml water and iron chloride and ammonia solution were added thereto as described in example 1. In this case 1954 mg (3.9 mmole) of $FeCl_3.6H_2O$ in 20 ml of water, 457 mg (2.3 mmole) of $FeCl_2.4H_2O$ in 20 ml of water and 15 ml of ammonia solution (25%) were added. The further treatment and the recovery of the particles were carried out as described in example 1.

The final particles contain magnetic iron oxide. The iron content in the particles was found to be 10.0%.

EXAMPLE 6

5 ml of dioctanoyl peroxide, 50 ml of water and 0.15 g of Na-laurylsulphate were homogenized to an emulsion with drops size 0.15-0.25 μm. This emulsion was mixed with a latex consisting of polystyrene particles having a diameter of 0.5-1.0 μm. The amount of latex that was added (40 ml) contained 5 ml of polystyrene particles and 35 ml of $H_2O$. After careful stirring for 24 hours, the mixture was transferred to a reactor containing 800 ml of water and 2.4 g of Na-laurylsulphate. 164 ml of methylmethacrylate, 140 ml of glycidylmethacrylate and 16 ml of ethylene glycoldimethacrylate were slowly added. After stirring for 2 hours 800 ml of $H_2O$ were added, and the temperature was raised to 60° C. After the polymerization a latex having a particle size of 2.4 μm and a solids content of 14.5% was obtained.

The treatment with ethylenediamine for introduction of the primary amino groups was carried out as described in example 1. Removal of unreacted ethylene diamine was carried out as in example 3.

Elementary analysis showed that the particles contained 4.5% N.

2.5 g dry particles treated with ethylene diamine were transferred to 20 ml of water. The particles were treated with iron chloride and ammonia solution as described in example 1. In this case 608 mg (2.3 mmole) of $FeCl_3.6H_2O$ in 20 ml of water, 249 mg (1.3 mmole) of $FeCl_2.4H_2O$ in 20 ml of water and 10 ml of ammonia solution (25%) were added.

The particles were recovered by filtration and washing with water and finally with methanol before drying.

After the treatment the particles contained magnetic iron oxide. The iron content was found to be 7.1%.

EXAMPLE 7

5 ml of dioctanoyl peroxide, 50 ml of water and 0.15 g of Na-laurylsulphate were homogenized to an emulsion with a drop size of 0.15-0.25 μm. This emulsion was mixed with a latex consisting of monodisperse polystyrene particles having a diameter of 0.53 μm (determined by electron microscopy). The amount of latex added (31.25 ml) contained 5 ml of polystyrene particles and 26.25 ml of $H_2O$. After careful stirring for 24 hours, the mixture was transferred to a reactor containing 800 ml of water and 2.5 g of Na-laurylsulphate. 304 ml of glycidylmethacrylate and 16 ml of ethylene glycoldimethacrylate were slowly added. After stirring for 2 hours 800 ml of $H_2O$ were added, and the temperature was raised to 60° C. After the polymerization a monodisperse latex having a particle size of 2.0 μm (determined by electron microscopy) and a solids content of 14.6% was obtained.

Treatment with ethylene diamine for introduction of primary amino groups was carried out as described in example 1. Removal or unreacted ethylene diamine was carried out as described in example 3. Elementary analysis showed that the particles contained 9.5% N.

2 g of dry particles treated with ethylene diamine were transferred to 20 ml of water. The particles were treated with iron chloride and ammonia solution as described in example 1. In this case 930 mg (3.4 mmole) of $FeCl_3.6H_2O$ in 20 ml of water, 390 mg (2.0 mmole) $FeCl_2.4H_2O$ in 20 ml of water and 15 ml of ammonia solution (25%) were added. The recovery of the particles was carried out as described in example 6. After the treatment the particles contain magnetic iron oxide. The iron content was found to be 12.5%.

EXAMPLE 8

5 ml of dioctyl adipate, 42.5 ml of water, 7.4 ml of acetone and 0.15 g of Na-laurylsulphate were homogenized to an emulsion with a drop size of 0.2-0.3 μm. This emulsion was mixed with a latex consisting of monodisperse polystyrene particles having a diameter of 1.04 μm (determined by electron microscopy). The amount of latex added (25 ml) contained 2.5 ml of polystyrene particles and 22.5 ml of $H_2O$. After careful stirring for 20 hours the acetone was removed by evaporation in vacuo, and the latex was transferred to a reactor containing 818 ml of $H_2O$ and 2.3 g of Na-laurylsulphate. A mixture of 270 ml of glycidyl methacrylate, 14 ml of ethylene glycoldimethacrylate and 5.7 g of benzoyl peroxide was added slowly under vigorous stirring. After stirring for 2 hours 818 ml of $H_2O$ were added, and the temperature was raised to 60° C. After the polymerization a monodisperse latex having a particle size of 5.0 μm (determined by electron microscopy) was obtained. Treatment with ethylene diamine for the introduction of primary amino groups was carried out as described in example 1. Removal of unreacted ethylene diamine was carried out as described in example 3. Elementary analysis showed that the particles contained 7.00% N.

3 g of particles treated with ethylene diamine were transferred to 25 ml of water. The particles were treated with iron chloride and ammonia solution as described in example 1. In this case 716 mg (2.6 mmole) of $FeCl_3.6H_2O$ in 25 ml of water, 301 mg (1.5 mmole) of $FeCl_2.4H_2O$ in 25 ml of water and 20 ml of ammonia solution (25%) were added.

The recovery of the particles was carried out as described in example 6. After the treatment the particles contain magnetic iron oxide. The iron content was found to be 7.0%.

EXAMPLE 9

10 ml of dioctanoyl peroxide, 85 ml of water, 15 ml of acetone and 0.30 g of Na-laurylsulphate were homogenized to an emulsion with a drop size of 0.2-0.3 μm. This emulsion was mixed with 37 ml of a latex consisting of monodisperse polymer/oligomer particles (in which each particle contained 70% oligomer styrene with molecular weight 2500 and 30% polystyrene) having a diameter of 1.0 μm (determined by Coulter Nano Sizer). The amount of latex added contained 4 ml of polymer/oligomer particles and 33 ml of $H_2O$. After careful stirring for 20 hours acetone was removed by evaporation in vacuo. The amount of latex after the removal of acetone, was 132 ml.

A mixture of 81.5 ml of glycidyl methacrylate, 122 ml of ethyleneglycol dimethacrylate, 314.5 ml of cyclohexanol, 1450 ml of $H_2O$ and 20 g of polyvinylpyrrolidone (molecular weight 360.000) was emulsified in an ultraturrax mixer for 1½ minute. The emulsion was transferred to a reactor, and the above latex residue of 132 ml was added. This mixture was stirred with a moderate stirring rate for 2 hours. Then 1450 ml of water were added, and the temperature was raised to 60° C. After the polymerization the reactor was cooled down, and cyclohexanol was removed by several times washing with water and isopropanol. After drying 155 g of monodisperse porous particles having a diameter of 4.8 μm (determined by electron microscopy) and a specific surface of 151 m$^2$/g polymer (BET) were obtained.

Treatment with ethylene diamine for the introduction of primary amino groups was carried out as described in example 5. Unreacted ethylene diamine was removed by centrifugation and several times washing with water. Elementary analysis of dry particles showed that they contained 4.9% N.

5 g of particles treated with ethylene diamine were transferred to 40 ml of water. The particles were treated with iron chloride and ammonia solution as described in example 1. In this case 1.50 g (5.5 mmole) of FeCl$_3$.6H$_2$O in 25 ml of water, 0.64 g (3.0 mmole) of FeCl$_2$.4H$_2$O in 25 ml of water and 25 ml of ammonia solution (25%) were added.

The recovery of the particles was carried out as in example 6. After the treatment the particles contain magnetic iron oxide The iron content was found to be 8.5%.

EXAMPLE 10

5 ml of dioctanoyl peroxide, 42.5 ml of H$_2$O, 7.5 ml of acetone and 0.15 g of Na-laurylsulphate were homogenized to en emulsion with a drop size of 0.2–0.4 μm. This emulsion was treated with a latex consisting of monodisperse polymer/oligomer particles having a diameter of 1.0 μm. The amount of latex added, 18.5 ml, contained 2 ml of polymer/ oligomer particles and 16.5 ml of H$_2$O. After careful stirring for 20 hours the acetone was removed by evaporation in vacuo, residue 66 ml. This residue was transferred to a reactor containing 800 ml of H$_2$O and 3.25 g of Na-laurylsulphate. A mixture of 40 ml of dimethylaminoethylmethacrylate, 90 ml of ethylene glycoldimethacrylate and 200 ml of cyclohexanol was added slowly under efficient stirring. After 2 hours 800 ml of water were added, and the temperature was raised to 60° C. After 6 hours of polymerization, the reactor was cooled and cyclohexanol was removed from the particles by several washings with H$_2$O and isopropanol. After drying there were obtained 110 g of monodisperse porous polymer particles having a diameter of 4.7 μm and a specific surface of 222 m$^2$/g polymer (BET). Elementary analysis showed that the polymer particles contained 1.7% N, 1.2 mmole of

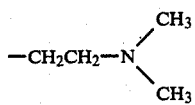

groups per g polymer.

5 g of particles were transferred to 50 ml water and treated with iron chloride and ammonia solution as described in example 1. In this case 1027 mg (3.8 mmole) of FeCl$_3$.6H$_2$O in 25 ml of water, 434 mg (2.2 mmole) of FeCl$_2$.4H$_2$O in 25 ml of water and 20 ml ammonia solution (25%) were added.

After the treatment was brought to an end, the particles were filtered from the solution and washed with water and finally with methanol. The particles were then dried.

After the treatment the particles contain magnetic iron oxide. The iron content was found to be 6.1%.

EXAMPLE 11

2 ml of Trigonox 21 S (t-butyl-peroxy-2-ethylhexanoate), 2 ml of dioctyladipate, 40 ml of water and 0.12 g of Na-laurylsulphate were homogenized to an emulsion with a drop size of 0.15–0.25 μm. This emulsion was mixed with a latex consisting of monodisperse polymer/oligomer particles having a diameter of 1.0 μm. The amount of latex added, 18.5 ml, contained 2 ml of polymer/oligomer particles and 16.5 ml of H$_2$O. After careful stirring for 24 hours the mixture was transferred to a reactor containing 700 ml of H$_2$O and 2.5 g of Na-laurylsulphate. A mixture of 33 ml of 4-vinylpyridine, 50 ml of divinylbenzene (50%) and 167 ml of toluene was slowly added. After vigorous stirring for 16 hours 1.5 g of Berol 292 (nonylphenol ethoxylate with 20 moles of ethylene oxide per mole nonylphenol) and 750 ml of water were added. The temperature was raised to 70° C., and polymerization was carried out until the reaction was complete.

After cooling the toluene was removed by several extractions with acetone. After drying 70 g of monodisperse porous polymer particles having av diameter of 4.7 μm and a specific surface of 193 m$^2$/g polymer (BET) were obtained. Elementary analysis showed that the particles contained 6.0% N.

654 mg (2.4 mmole) of FeCl$_3$.6H$_2$O were dissolved in 25 ml of water and cooled to 10° C. Similarly, 274 mg (1.4 mmole) of FeCl$_2$.4H$_2$O were dissolved in 25 ml of water and cooled to 10° C. These two solutions were combined, and then 50 ml of methanol precooled to 10° C. were added. To this mixture 1 g of dry particles was added, and it was all transferred to a rotating container which was evacuated to 10 mm Hg. After 30 minutes 10 ml cold (10° C.) ammonia solution (25%) were added by suction. The vacuum was then eliminated, and the temperature was raised to 80° C. After 15 minutes at 80° C. the mixture was cooled and the particles filtered off. The particles were washed with water and finally with methanol and were then dried. After the treatment the particles contain magnetic iron oxide. The iron content was found to be 16.4%.

EXAMPLE 12

5 ml of dioctanoyl peroxide, 42.5 ml of water, 7 ml of acetone and 0.15 g of Na-laurylsulphate were homogenized to an emulsion with a drop size of 0.2–0.3 μm. This emulsion was mixed with a latex consisting of monodisperse polystyrene particles having a diamter of 0.53 μm. The amount of latex added (20.83 ml) contained 3.33 ml of polystyrene particles and 17.50 ml of H$_2$O. After careful stirring for 20 hours acetone was removed in vacuo and the latex transferred to a reactor containing 800 ml of water and 3.25 g of Na-laurylsulphate. A mixture of 100 ml of divinylbenzene (50%) and 200 ml of toluene was slowly added. After vigorous stirring for 16 hours 800 ml of H$_2$O and 4.0 g of Berol 292 (nonylphenol ethoxylate with 20 moles of ethylene oxide per mole nonylphenol) were added. The temperature was raised to 70° C. and polymerization was carried out until the reaction was complete.

After cooling toluene was removed by several extractions with acetone. After drying 82 g of monodisperse porous particles having a diameter of 2.0 μm and a specific surface of 472 m²/g polymer (BET) were obtained.

5 g of dry particles were transferred to a mixture of 50 ml of concentrated nitric acid and 125 ml of concentrated sulphuric acid in 30 minutes under stirring. 40 minutes after the addition of the particles was brought to an end, the reaction mixture was poured into a container containing 1 liter of ice. The particles was filtered from the solution and washed with water (400 ml) and finally with methanol (200 ml). After drying 5 g of the particles were transferred to a rotating container together with 10 g of FeSO₄.7H₂O dissolved in 150 ml of water. The container was then evacuated to 10 mm Hg. After 45 minutes 50 ml of ammonia solution (25%) were added by suction. Then the vacuum was eliminated, and the temperature was raised to 80° C. After 15 minutes at 80° C. the mixture was cooled and filtered. First the particles were washed with water (400 ml) and then finally with methanol (200 ml). The particles were then dried. After this treatment the particles contain magnetic iron oxide. The iron content in the particles was found to be 20.0%.

EXAMPLE 13

Monodisperse porous particles were prepared as described in example 12.

5 g of porous particles, 1 g of polyamine amide (Versamid-115) and 100 ml of toluene were mixed and transferred to a rotating container which was then evacuated (10 mm Hg). The temperature in the mixture was kept between 5 and 10° C. After one hour the temperature was raised and the mixture evaporated to dryness.

2 g of these particles in 40 ml of methanol were then treated with iron chloride and ammonia solution as described in example 1 to form ferromagnetic ironoxide in the particles. In this case 520 mg (1.9 mmole) of FeCl₃.6H₂O in 25 ml of water, 220 mg (1.1 mmole) FeCl₂.4H₂O in 25 ml of water and 10 ml of ammonia solution (25%) were added.

The particles were separated from the solution by filtration, washed with water and then finally with methanol. The particles were then dried. The final particles contain magnetic iron oxide. The iron content was found to be 5.2%.

EXAMPLE 14

To a reactor fitted with stirrer of the impeller type 1800 ml of water, 4.8 g of Gelvatol 20-60 (polyvinyl alcohol 80% hydrolyzed) and 0.012 g of Na-laurylsulphate were added. To this a mixture consisting of 80 ml of styrene, 120 ml of divinylbenzene (50%), 200 ml of heptane, 200 ml of toluene and 3 g of azobisisobutyronitrile was added. This was vigorously stirred for 30 minutes before the temperature was raised to 70° C. The polymerization took place under vigorous stirring for 5 hours. After cooling the polymer was filtered from the aqueous phase, and toluene/heptane was removed by extraction several times with acetone. After drying there were obtained 180 g of a porous powder having a particle size of 5–50 μm and a specific surface of 234 m²/g.

For the introduction of NO₂ groups and the subsequent treatment with 2- and valent iron to magnetize the particles, the same method as described in example 12 was used.

After the treatment the particles contained magnetic iron oxide. The iron content was found to be 17.3%.

EXAMPLE 15

To a reactor fitted with a blade stirrer 225 ml of water and 0.6 g of Gelvatol 20-60 (polyvinylalcohol 80% hydrolyzed) were added. A mixture consisting of 10 ml of 3-nitrostyrene, 15 ml of divinylbenzene (75%), 25 ml of toluene, 25 ml of heptane and 0.375 g of azobisisobutyronitrile was added thereto. This was subjected to vigorous stirring for 30 minutes before the temperature was raised to 70° C. The polymerization was carried out under vigorous stirring until the reaction was complete. After cooling the polymer was filtered from the aqueous phase and toluene was removed by extraction several times with acetone. After drying there were obtained 23 g of a porous powder having a particle size of 10–60 μm and a specific surface of 254 m²/g (BET).

1 g of these porous particles was transferred to a rotating container together with 1.4 g of FeSO₄.7H₂O dissolved in 40 ml of water. The container was then evacuated to 10 mm Hg. After 45 minutes 10 ml of ammonia solution (25%) were added by suction. The vacuum was then eliminated, and the temperature was raised to 80° C. After 15 minutes at 80° C. the mixture was cooled and filtered. First the particles were washed with water (100 ml) and finally with methanol (25 ml). The particles were then dried. After this treatment the particles contain magnetic iron oxide. The iron content in the particles was found to be 19.8%.

EXAMPLE 16

5.0 ml of dioctanoyl peroxide, 42.5 ml of H₂O, 7.5 ml of acetone and 0.15 g of Na-laurylsulphate were homogenized to an emulsion with a drop size of 0.2–0.4 μm. This emulsion was treated with 15.72 ml of a latex consisting of monodisperse polystyrene particles having a diameter of 0.46 μm (determined by electron microscopy). The amount of latex added contained 2.5 ml of polystyrene particles and 13.22 ml of H₂O. After careful stirring for 20 hours the acetone was evaporated in vacuo, and the latex was transferred to a reactor containing 800 ml of H₂O and 3.0 g of Na-laurylsulphate. A mixture of 201.6 ml of methylmethacrylate, 22.4 ml of ethylene glycoldimethacrylate and 96.0 ml methacrylic acid was added slowly with good stirring. After stirring for 1 hour 800 ml of H₂O were added, and the temperature was raised to 65° C. After polymerization for 2 hours 1.6 g of Berol 292 were added. The polymerization was continued until the reaction was complete, and a monodisperse latex having a particle size of 2.3 μm (determined by electron microscopy) was obtained.

For further treatment the particles were separated from the aqueous phase by centrifugation. The particles were washed with acetone and dried. 2 g of the dry particles were then transferred to 50 ml of a sodium hydroxide solution (2%) in a glass flask fitted with a stirrer. After stirring for 20 minutes the particles were separated from the solution by centrifugation. Alternate washing with water and centrifugation were then carried out until the washings had an approximately neutral pH. The particles were then transferred to 50 ml of water and treated with iron chloride and ammonia solution as described in example 1. In this case 334 mg (1.3 mmole) of FeCl₃.6H₂O in 20 ml of water, 145 mg (0.7 mmole) of FeCl₂.4H₂O in 20 ml of water and 10 ml of ammonia solution (25%) were added. The recovery of the particles was carried out as in example 6. After the treatment the particles contain magnetic iron oxide. The iron content was found to be 5.2%.

EXAMPLE 17

Porous, monodisperse particles having a diameter of 2.0 μm prepared as described in example 12 were treated with chloromethyl ether, ClCH$_2$OCH$_3$, in a known manner for the introduction of —CH$_2$Cl on the benzene nucleus. By this treatment porous particles with 1.2 mmole —CH$_2$Cl groups per g particles were obtained.

100 ml of polyethylene glycol, HO(CH$_2$CH$_2$O)$_n$H, with mean n=30, 100 ml of tetrahydrofurane and 1.5 g of NaH were mixed in a three-necked flask under an atmosphere of nitrogen and were kept stirring at 50° for 2 hours. 10 g of the chloromethylated particles prepared above were added, and it was heated with reflux for 2 days. After the reaction was brought to an end, the particles were separated off by filtration and they were washed several times with tetrahydrofuran. Finally, the particles were dried in vacuo.

2.8 g of the dry particles were treated with iron chloride and ammonia as described in example 1. In this case 1300 mg (4.8 mmole) FeCl$_3$.6H$_2$O and 450 mg (2.4 mmole) FeCl$_2$.4H$_2$O were used.

The particles were separated from the solution by filtration and were washed with water and finally with methanol. The particles were then dried. After the treatment the particles contain magnetic iron oxide. The iron content was found to be 10.5%.

EXAMPLE 18

Porous, monodisperse particles having a diameter of 2.0 μm prepared as described in example 12, were treated according to known methods, with chloromethylphthalimide,

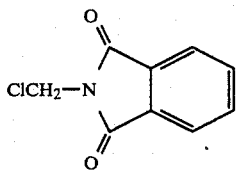

and then with hydrazine for introduction of —CH$_2$NH$_2$ groups on the benzenenucleus. A product containing 1.3 mmole —CH$_2$NH$_2$ groups per g of the particles was prepared. 5 g of dry particles were treated with 20 g of epoxy-polyethylene glycolmonomethylether,

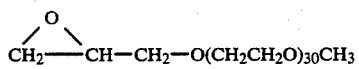

and the mixture was kept under an atmosphere of nitrogen with careful stirring in a three-necked flask at 90° for 24 hours. The particles were then separated by filtration, and washed several times with tetrahydrofurane until all extractable material was removed, and were then dried.

2.8 g of the dry particles were treated with iron chloride and ammonia as described in example 1. In this case 1300 mg FeCl$_3$.6H$_2$O and 450 mg FeCl$_2$.4H$_2$O were used.

The particles were separated from the solution by filtration, washed with water and finally with methanol. The particles were then dried. After the treatment the particles contain ferromagnetic iron oxide. The iron content was found to be 10%.

EXAMPLE 19

To 100 ml of an acetone solution containing 6.2 mmoles of FeCl$_3$ and 3.1 mmoles of FeCl$_2$ there were added 3 g of dry, porous monodisperse particles having polyethylene oxide groups bonded to the benzene nucleus. The preparation of the particles is described in example 18.

The suspension of the particles in acetone was stirred for 30 minutes under an atmosphere of nitrogen. The particles were then filtered off on a suction funnel while all the time a blanket of nitrogen was kept covering the filter cake. When all excess liquid was removed, the particles were treated with a flow of moist NH$_3$ vapor. The particles were then washed with water and finally with methanol. The particles then were dried. After the treatment the particles contain magnetic iron oxide. The iron content was found to be 9.5%.

EXAMPLE 20

A linear polyamide was prepared by known methods from equimolar amounts of 1,11-diamino-3,6,9-trioxaundecane NH$_2$—CH$_2$—CH$_2$—(OCH$_2$CH$_2$)$_3$NH$_2$ and sebacic acid dichloride

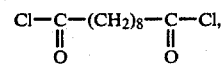

by dissolving the two reactants in water and carbon tetrachloride respectively, and carrying out an interfacial polymerization.

10 g of purified polyamide dissolved in 100 ml of methylene chloride, 200 ml of H$_2$O and 0.3 g of cetylpyridinium bromide were homogenized to a drop size of 0.3–2 μm. Methylene chloride was then removed by evaporation in vacuo.

10 ml of an aqueous dispersion containing 1.6 g of polyamide particles were treated with iron chloride and ammonia as described in example 1. In this case 1000 mg of FeCl$_3$.6H$_2$O and 350 mg of FeCl$_2$.4H$_2$O were used.

The particles were separated from the solution by filtration, washed with water and finally with methanol. The particles were then dried. After the treatment the particles contain magnetic iron oxide. The iron content was found to be 11.5%.

EXAMPLE 21

5.0 ml of dioctanoyl peroxide, 42.5 ml of H$_2$O, 7.5 ml of acetone and 0.15 g of Na-laurylsulphate were homogenized to an emulsion with a drop size of 0.2–0.4 μm. This emulsion was combined with 23.1 ml of a latex consisting of monodisperse polystyrene particles having a diameter of 0.95 μm. The amount of latex added contained 2.5 ml of polystyrene particles and 20.6 ml of H$_2$O. After careful stirring for 24 hours the acetone was evaporated in vacuo. The amount of latex after removal of the acetone was 71 ml.

A mixture of 52 ml of hydroxyethylmethacrylate, 78 ml of ethylene glycoldimethacrylate, 200 ml of cyclohexanol, 800 ml of water and 10 g of Pluronic F 68 (polyetylene oxide derivative) was emulsified with the ultraturrax mixer for 1½ min. The emulsion was transferred to a reactor and the above latex residue of 71 ml was added. This mixture was stirred at a moderate rate for 2 hours. 800 ml of water was then added and the temperature was raised to 60° C. After the polymerization the reactor was cooled and cyclohexanol removed by several washings with water and isopropanol. After drying 125 g of monodisperse porous particles having a diameter of 4.0 μm and a specific surface of 128 m²/g (BET) were obtained.

1.5 g of the dry particles were treated with a mixture of 25 ml of concentrated nitric acid and 65 ml of concentrated sulphuric acid with stirring for 1 hour. The mixture was then poured into a container containing 1 litre of ice. The particles were filtered off and washed until pH in the washings was neutral. After drying the particles were transferred to a rotating container together with 2.06 g of FeSO$_4$.7H$_2$O dissolved in 25 ml of water. The mixture was rotated for 30 minutes under an atmosphere of N$_2$. 10 ml of ammonia solution (25%) was then added by suction. The temperature was then raised to 80° C. After 15 minutes at 80° C. the mixture was cooled and filtered. The particles were washed several times with water and methanol. After this treatment the particles contain magnetic iron oxide. The iron content in the particles was found to be 18.4%.

EXAMPLE 22

Monodisperse porous particles prepared as described in example 21 were used. The particles had a diameter of 4.0 μm and a specific surface of 128 m²/g.

1 g of dry particles were added to 7.5 g NaNO$_2$ dissolved in 15 ml of water under vigorous stirring with a magnetic stirrer. The mixture was then cooled to 0° C. in an ice bath. For a period of 50 minutes 10 ml of concentrated hydrochloric acid were added dropwise. Then the mixture was heated to 20° C. in 3 hours. The mixture was poured onto 40 g of ice and filtered. Washing was carried out with 1 M Na-carbonate solution until the filtrate was neutral and then several times with water.

After drying 0.87 g of particles were added to a solution of 1 g of FeSO$_4$.7H$_2$O dissolved in 30 ml of water. The mixture was bubbled through with N$_2$ (99.99%) and the mixture was rotated for 30 minutes under an atmosphere of N$_2$. Then 10 ml of ammonia solution (25%) was added by suction. Under a continued atmosphere of N$_2$ the temperature was raised to 80° C. After 10 minutes at 80° C. the mixture was cooled and filtered. After washing several times with water, the particles were dried at 60° C. After this treatment the particles contain magnetic iron oxide. The iron content in the particles was found to be 12.3%.

EXAMPLE 23

Monodisperse porous particles prepared as described in example 9 were used. The particles had a dimeter of 4.8 μm and a specific surface of 151 m²/g, and after treatment with ethylene diamine the particles contained 4.9% N.

1 g of dry particles was mixed with 834 mg of FeSO$_4$.7H$_2$O (3 mmole) dissolved in 40 ml of water. The mixture was rotated for 30 minutes under an atmosphere of N$_2$. 10 ml of concentrated ammonia solution (25%) were then added by suction. The temperature was then raised to 80° C. with a light suction of air through the apparatus. After 15 minutes at 80° C. the mixture was cooled and the particles were washed several times with water and finally dried. After this treatment the particles contain magnetic iron oxide. The iron content in the particles was found to be 10.5%.

EXAMPLE 24

Monodisperse, porous polymer particles with amino groups were used, prepared as described in example 9. The particles had a diameter of 4.8 μm, and after treatment with ethylene diamine the particles contained 4.9% N.

1 g of dry particles was added to 243 mg of FeCl$_3$.6H$_2$O (0.92 mmole) dissolved in 15 ml of H$_2$O and 129 mg of CoSO$_4$.7H$_2$O (0.46 mmole) dissolved in 30 ml of H$_2$O. The mixture was rotated in a film evaporator at 25° C. in vacuo for 10 minutes. Then the vacuum was eliminated and the rotation of the mixture was continued at 90° C. for 15 minutes. 30 ml of 6 N NaOH were then added. Heating was continued at 90° C. for 1 hour. The particles were then cleaned by several washings with water and finally dried. After this treatment the particles contain a magnetic material. Analyses of the particles show a content of 4.4% Fe and 2.3% Co.

EXAMPLE 25

Monodisperse porous particles with nitro groups were used, prepared as described in example 12. The particles had a diameter of 2.0 μm and after nitration they contained 8.8% N.

2 g of dry particles were added to 1.6 g of FeSO$_4$.7H$_2$O (5.75 mmole) dissolved in 25 ml of H$_2$O and 0.8 g of CoSO$_4$.7H$_2$O (2.84 mmole) dissolved in 40 ml H$_2$O. The mixture was rotated in a film evaporator at 25° C. under an atmosphere of N$_2$ for 30 minutes. 25 ml of 3 N NaOH were then added and it was heated at 80° C. for 1 hour under an atmosphere of N$_2$. After this treatment the particles contain a magnetic material. Analyses of the particles showed a content of 11.5% Fe and 6.1% Co.

EXAMPLE 26

Monodisperse polymer particles with amino groups were used, prepared as described in example 7. The particles had a diameter of 2.0 μm and after treatment with ethylene diamine they contained 9.5% N.

1 g of dry particles was transferred to 20 ml of water and 243 mg of FeCl$_3$.6H$_2$O (0.92 mmole) dissolved in 15 ml of H$_2$O and 91 mg of MnCl$_2$.4H$_2$O (0.46 mmole) dissolved in 15 ml of H$_2$O were added. The mixture was rotated in a film evaporator at 25° C. in vacuo for 10 minutes. 20 ml of 3 N NaOH were then added, and it was heated at 90° C. for 1 hour under an atmosphere of N$_2$. The particles were then cleaned by washing several times with water and finally drying.

After this treatment the particles contain a magnetic material. Analyses of the particles showed a content of 4.3% Fe and 2.2% Mn.

EXAMPLE 27

5 ml of dioctanoyl peroxide, 42.5 ml of H$_2$O, 7.5 ml of acetone and 0.15 g of Na-laurylsulphate were homogenized to an emulsion with a drop size of 0.2–0.4 μm. This emulsion was combined with 28 ml of a latex consisting of monodisperse polystyrene particles having a diameter of 2.0 μm. The amount of latex added contained 2.27 ml of polystyrene particles and 25.73 ml of H$_2$O.

After careful stirring of this mixture for 24 hours all the dioctanoyl peroxide added were taken up in the polystyrene particles. Acetone was then removed by evaporation in vacuo, and there was obtained a residue of 75.5 ml of latex containing 7.27 ml of polystyrene-dioctanoyl peroxide particles. A mixture of 800 ml of water, 0.6 g of Na-laurylsulphate, 12 g of polyvinylpyrrolidone (MW 360 000), 60 ml of ethylacrylate, 90 ml of divinyl benzene (50%) and 150 ml of cyclohexanol was homogenized by means of a ultra turrax mixer. The mixture was transferred to a reactor, and the above latex of 75.5 ml was then added. The reactor was then closed and stirring was continued at 25° C. for 20 hours. Then 800 ml of $H_2O$ were added, and the reactor was heated to 60° C. Polymerization was carried out for 2 hours at 60° C. and then for 5 hours at 70° C. until the reaction was complete. After washing the product with water and isopropanol, filtration and drying there was obtained a powder consisting of monodisperse macroporous polymer particles having a diameter of 9.8 μm.

5 g of dry particles were mixed with 50 ml of diethylenetriamine in a small three-necked flask fitted with stirrer and a short fractionating column. The temperature was gradually raised to 200° C. The heating was continued for 5 hours. Ethyl alcohol distilled off through the column. After dilution with water the particles were purified by filtration and several times washing with water and finally drying. Elementary analysis showed that the particles contained 3.2% N.

2 g of the particles were transferred to 20 ml of water and treated with iron chloride and ammonia solution as described in example 1. In this case 690 mg (2.55 mmole) $FeCl_3.6H_2O$ in 25 ml of water and 288 mg (1.45 mmole) of $FeCl_2.4H_2O$ in 25 ml of water were used, and 20 ml of ammonia solution (25%) were added.

After the treatment was brought to an end, the particles were filtered from the solution and washed with water and finally with methanol. The particles were then dried. After this treatment the particles contain magnetic iron oxide. The iron content was found to be 9.5%.

We claim:

1. A process for the preparation of magnetic polymer particles which comprises:
   mixing in the substantial absence of oxygen:
   (i) a solution of Fe(II) salts alone or in combination with salts of other metals which are capable of forming magnetic oxides upon oxidation,
   (ii) an aqueous dispersion of filterable polymer particles having a particle size above about 0.2 μ and containing groups which are capable of oxidizing Fe(II) compounds in basic solution entirely or partially to Fe(III) compounds, and
   (iii) a base to increase the pH, whereby the groups of said polymer particles will wholly or partly oxidize said Fe(II) compounds to form substantially insoluble Fe compounds on and in said polymer particles,
   said process of oxidation leading to a continuous transport of Fe(II) compounds from solution on and into said polymer particles.

2. The process according to claim 1 wherein said groups capable of oxidizing Fe(II) are $NO_2$ groups which have been introduced into the monomer from which said polymer particles are produced or into said polymer particles prior to treatment with Fe(II) salts and base.

3. The process according to claim 1 wherein said groups capable of oxidizing Fe(II) are $ONO_2$ or ONO, said groups being introduced into said polymer particles before treatment with said Fe(II) salts and base.

4. The process according to claim 1 wherein the base (iii) is ammonia.

5. The process according to claim 1 wherein the polymer particles are cross-linked.

6. The process according to claim 1 wherein porous macroreticular particles are employed, said particles being prepared by copolymerization of a monomer mixture of styrene, styrene derivatives or acrylates and divinyl benzene or di- or triacrylates in the presence of inert solvents for the monomers.

7. The process according to claim 1 wherein magnetic particles are heated after formation.

8. The process according to claim 1 wherein porous macroreticular particles prepared by copolymerization of styrene and divinyl benzene are treated with $HNO_3$ or a mixture of $HNO_3$ and $H_2SO_4$ to introduce $NO_2$ groups therein.

9. Magnetic, monodisperse polymer particles produced in accordance with the process of claim 1 having a standard deviation of <5%.

* * * * *

UNITED STATES PATENT AND TRADEMARK OFFICE
CERTIFICATE OF CORRECTION

PATENT NO. : 4,654,267
DATED : March 31, 1987
INVENTOR(S) : John Ugelstad et al It is certified that error appears in the above-identified patent and that said Letters Patent is hereby corrected as shown below:

On the title page, please change item [30] Foreign Application Priority Data, for the Norweigan Application 823748 from "Nov. 16, 1982" to --Nov. 10, 1982--.

Signed and Sealed this

Twenty-third Day of March, 1993

Attest:

STEPHEN G. KUNIN

*Attesting Officer*      Acting Commissioner of Patents and Trademarks